US006371331B1

(12) United States Patent
Göhde et al.

(10) Patent No.: US 6,371,331 B1
(45) Date of Patent: Apr. 16, 2002

(54) ELECTRONIC APPARATUS FOR DISPENSING PRECISE SMALL QUANTITIES OF FLUID

(75) Inventors: Wolfgang Göhde, Nottuln; Armin Akbari, Münster, both of (DE)

(73) Assignee: Partec Partikelzahlgerate GmbH, Munster (DE)

( * ) Notice: Subject to any disclaimer, the term of this patent is extended or adjusted under 35 U.S.C. 154(b) by 0 days.

(21) Appl. No.: 09/646,239
(22) PCT Filed: Mar. 15, 1999
(86) PCT No.: PCT/EP99/01673
  § 371 Date: Sep. 14, 2000
  § 102(e) Date: Sep. 14, 2000
(87) PCT Pub. No.: WO99/47906
  PCT Pub. Date: Sep. 23, 1999

Related U.S. Application Data
(60) Provisional application No. 60/078,140, filed on Mar. 16, 1998.

(51) Int. Cl.[7] .................................................. G01N 1/00
(52) U.S. Cl. ...................... 222/55; 222/132; 222/144.5; 222/394; 222/422; 222/63; 222/67; 222/141; 222/130
(58) Field of Search .......................... 222/55, 129, 132, 222/135, 144.5, 394; 141/130; 422/63–65, 67

(56) References Cited

U.S. PATENT DOCUMENTS

| 3,994,423 A | 11/1976 | Burg .......................... 222/420 |
| 5,389,339 A | 2/1995 | Petschek et al. .............. 422/64 |
| 5,654,199 A | 8/1997 | Copeland et al. ............. 436/46 |

FOREIGN PATENT DOCUMENTS

| DE | 1 903 077 | 9/1970 |
| EP | 0 753 750 A2 | 1/1997 |

*Primary Examiner*—J. Casimer Jacyna
(74) *Attorney, Agent, or Firm*—Rankin, Hill, Porter & Clark LLP (57) ABSTRACT

An apparatus for dispensing a measured quantity of a liquid has a container holding a quantity of liquid to be measured and dispensed and a conduit with an inlet end, an outlet end and a measuring section having a known volume. A sensor determines when the measuring section contains liquid. A passage with a first valve is provided for delivering liquid from the container to the conduit inlet end and air under pressure urges liquid from the container to the conduit. A source of air under pressure is connected to the conduit and a second valve controls delivery of air to the conduit from the source. A control connected to the sensor and to the first and second valves sequentially closes the second valve and opens the first valve to cause flow of liquid from the container to the conduit until the sensor determines that the measuring section contains liquid, and then closes the first valve and opens the second valve to admit air to the conduit, thereby expelling a measured quantity of liquid from the outlet end.

3 Claims, 8 Drawing Sheets

|   | 1 | 2 | 3 | 4 | 5 | 6 | 7 | 8 | 9 | 10 | 11 | 12 | 13 | 14 |
|---|---|---|---|---|---|---|---|---|---|----|----|----|----|----|
| A | X |   |   |   |   |   |   |   |   |    |    |    |    |    |
| B | X | X | X |   |   |   |   |   |   |    |    |    |    |    |
| C |   |   | X |   |   |   |   |   |   |    |    |    |    |    |
| D |   |   | X | X | X |   |   |   |   |    |    |    |    |    |
| E | X |   |   |   | X |   |   | X |   | X  |    |    | X  |    |
| F |   |   |   |   |   |   | X |   |   |    |    | X  | X  |    |
| G |   |   |   |   |   | X |   | X |   |    |    |    |    |    |
| H |   |   |   |   |   |   |   | X |   |    | X  | X  | X  | X  |
| I | X |   | X |   | X |   |   |   |   |    |    |    |    |    |
| J |   | X |   | X |   | X |   |   |   |    |    |    |    |    |
| K | X | X |   |   |   |   |   |   |   |    |    |    |    |    |
| L |   |   | X | X |   |   |   |   |   |    |    |    |    |    |
| M |   |   |   | X | X |   |   |   |   |    |    |    |    |    |
| N |   |   |   |   | X | X |   |   |   |    |    |    |    |    |
| O |   |   |   |   |   |   |   |   | X |    |    |    |    |    |
| P |   |   |   |   |   |   |   |   |   | X  |    |    |    |    |
| Q |   |   |   |   |   |   |   |   |   |    | X  |    |    |    |
| R |   |   |   |   |   |   |   |   |   | X  |    |    |    |    |
| S |   |   |   |   |   |   |   |   |   | X  |    |    |    |    |

ELECTRONIC APPARATUS FOR DISPENSING PRECISE SMALL QUANTITIES OF FLUID

This application claims benefit of provisional 60/078,140 filed Mar. 16, 1998.

This is a 371 of International Application PCT/EP99/01673, with an international filing date of Mar. 15, 1999.

FIELD OF THE INVENTION

This invention relates to an apparatus for dispensing precisely measured small quantities of fluid and, more particularly, to dispensing such fluid quickly and with high accuracy and repeatability, particularly for chemical analysis purposes.

BACKGROUND OF THE INVENTION

For purposes of analyzing fluids, particularly body fluids such as blood or urine, to evaluate the condition of the fluids and detect the presence of diseases, it is common practice to add to small quantities of the body fluids other chemicals which may react with the fluids in such a way that the fluids can be analyzed by an electro-mechanical analyzing machine such as a particle analyzing system sold by Partec GmbH, Muenster, Germany under the trademark Partec PAS II. For example, a sample of blood taken from a patient is divided into several parts, each typically being about 100 $\mu$l (microliters) in volume. To each sample may be added three or more chemicals such as monoclonal antibodies of different types an possibly other strains or reagents, the resulting combinations are stirred and allowed to incubate for a selected interval of time. The process of adding these chemicals is usually referred to as pipetting. The resulting mixture is then ready to be pumped into the analyzer which provides information about the numbers of particles, their condition, etc. in ways which are well known per se. The resulting mixture may also be subjected to other forms of analysis, depending upon the kind of condition which is being sought.

There are several problems associated with this process. Because of the fact that the body fluids, particularly blood or serum, can carry viral and other substances which are dangerous to the individuals performing the analysis, efforts have been made to enclose the fluids so that the workers are not exposed to these fluids. In addition, efforts have been made to automate the processes to further reduce exposure and also improve the accuracy and precision of the chemical additions, partly to minimize the occasional human error.

One such effort involves the use of programmed, robotic arms which essentially mimic the motion of a human arm. A rack of test tubes containing fluids to be analyzed is placed in the vicinity of a programmed titrating machine, the tubes being arranged in the rack in a carefully selected order. Vials of additives such as monoclonal antibodies and other reagent materials are then placed in locations accessible to the machine arm. An arm, which carries a titrating tip, then goes through the same process as would be performed manually by a human operator: the tip is inserted into a vial containing one of the additives and sucks in a small quantity of additive. The arm then moves to the appropriate one of the test tubes and injects the additive into the tube. Before taking the next additive, the titrating tip must be washed. The arm then goes to the next additive, transfers a small quantity to the next test tube, is washed, and so on until all of the test tubes have received the desired quantities of the additives.

A system such as this has the advantage over manual operations that human error is reduced and the quantities of additives added to the various test tubes is reasonably accurate, i.e., within about 20%. The process can also be made more efficient by adding a first additive to all of those test tubes designated to receive that additive before washing and going on to the next one. All of this is under computer control, the computer being programmable to designate which tubes are to receive which additives.

However, the system also has serious disadvantages. In particular, it is not possible to effectively operate such a system with the vials and other apparatus closed in such a way that workers in the vicinity are isolated from the substances in the test tubes or other apparatus. Thus, if dangerous substances may, or are known to, be present, the workers themselves must be protected with special isolation clothing.

In addition, much time is consumed by this process. With a rack of thirty-six test tubes and four or five additives with different permutations of additives designated for the tubes, the machine can take hours to complete the process. Even with complex machines using two or three arms concurrently, which appears to be the practical maximum, the process can take one and one-half hours. In addition, the need to wash the titrators involves considerable waste of expensive materials. The monoclonal antibodies, in particular, are quite expensive and each washing necessitates that some of this valuable material is lost. Also, if dangerous substances such as radioactive markers are used, the washing step requires that special care to be taken in disposing of the waste water. Still further, the mechanical apparatus involved in an arm system requires long rapid movements, placing significant demands on the equipment which must be maintained. The apparatus is rather fragile and maintenance is a significant expense and removes the equipment from use at regular intervals. No other reasonably efficient automated system is known to exist.

Pipetting is also used in fields other than laboratory medicine, such as other chemical processes, food production and processing and fermentation technology. The amounts of liquid handled in these fields varies from very small up to large amounts of liquid, e.g., from amounts measured in microliters to liters. For the larger amounts, pipetting is not generally used, but for the smaller amounts, particularly in a laboratory context, it is very common.

SUMMARY OF THE INVENTION

Briefly described, the invention comprises an apparatus for dispensing a measured quantity of a liquid comprising a container holding a quantity of liquid to be measured and dispensed, a conduit having an inlet end and an outlet end and including a measuring section having a predetermined volume and a dispensing tip at the outlet end, and sensor means for determining when the measuring section contains liquid. A passage is provided for delivering liquid from the container to the conduit inlet end. A source of air under pressure urges liquid from the container to the conduit. A first valve is in the passage. A source of air under pressure is connected to the conduit. A second valve controls delivery of air to the conduit from the source. Control means connected to the sensor means and to the first and second valves sequentially closes the second valve and opens the first valve to cause flow of liquid from the container to the conduit until the sensor means determines that the measuring section contains liquid, and then closes the first valve and opens the second valve to admit air to the conduit, thereby expelling a measured quantity of liquid from the dispensing tip.

BRIEF DESCRIPTION OF THE DRAWINGS

In order to impart full understanding of the manner in which the advantages and features of the invention are attained in accordance with the invention, particularly advantageous embodiments thereof will be described with reference to the following drawings, which form a part of this disclosure, and wherein.

DESCRIPTION OF PREFERRED EMBODIMENTS

Figure 1:
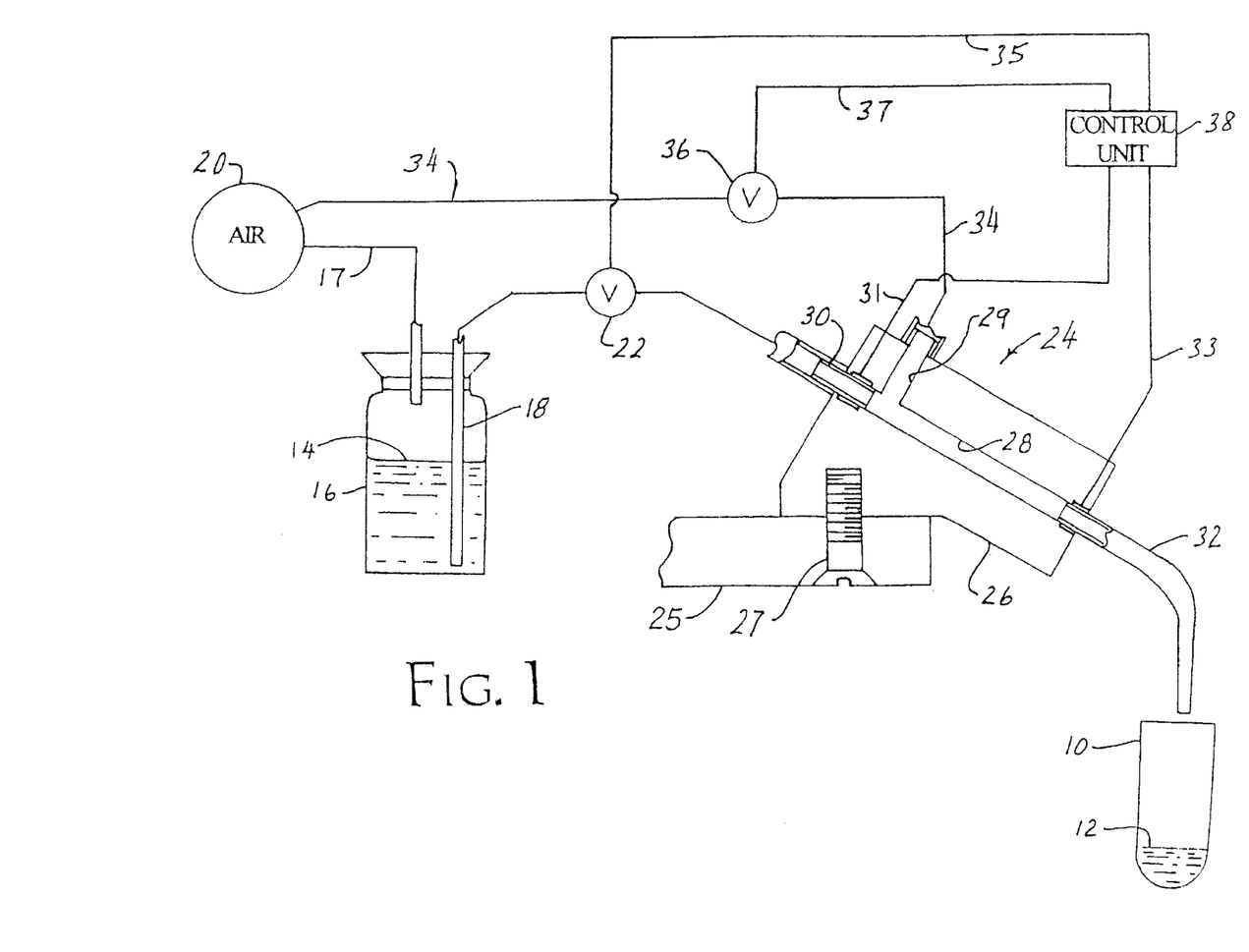
FIG. 1 is a schematic side elevation, in section, of a dispensing device and associated apparatus in accordance with the invention.

FIG. 1 shows the details of a first embodiment of a dispensing device which is usable in a system for adding multiple fluids to a test tube or vial 10. The system will be described in the context of a system for analyzing blood, although as suggested above, it is usable in systems for other purposes. As indicated in the figure, vial 10 contains a sample of body fluid such as blood 12 which has been added to the vial using a conventional technique. A reservoir of an additive material 14 is provided in a stoppered container 16 which has an output tube 18 reaching near the bottom of container 16 forming a passage for delivering liquid from the container. A source 20 of air under substantially constant pressure has an output 17 tube connected through the stopper of container 16 so that the contents of the container are under pressure. An electrically controllable valve 22 is connected in tube 18 to control the flow of liquid 14 through tube 18.

A dispenser indicated generally at 24 comprises a body 26 of electrically non-conductive material having conduits 28 and 29 formed therein. Body 26 is supported on a flange 25 and can be attached thereto by a fastener 27. Conduit 28 extends entirely through the body and conduit extends inwardly from a surface of the body and communicates with conduit 28. An inlet end of conduit 28 has a connection pipe 30 which is made of a good electrical conducting material such as platinum. Pipe 30 is connected to tube 18 for delivering liquid into conduit 28 when valve 22 is open. At an outlet end of conduit 28 is an output pipe 32 for delivering fluid from conduit 28 to vial 10. Pipe 32 is preferable made of the same material as pipe 30.

Conduit 29 is connected to a tube 34 which has an electrically controllable valve 36 therein and which is connected to an output of an air pressure source such as source 20, although the source of air need not be the same as that used for pressurizing container 16. Valves 22 and 36 are independently controlled in a manner to be described. A fail-safe mode can be provided in which both valves are closed in the event, for example, of power loss. These valves can be pinch valves or valves of any type commonly used in chemical equipment which are electrically controllable to pen and close in response to small control signals with rapid response times. A pinch valve operates by squeezing a liquid conveying elastic tube to stop flow and then releasing the pinched tube to permit it to recover its original shape and fluid-carrying capability.

Pipes 30 and 32 are provided with electrical connections 31 and 33, respectively, which are electrically connected to a control unit 38 which responds to a change in an electrical characteristic of substances between the two pipes and produces control signals on conductors 35 and 37 in response to that change. The control signals are connected to valves 22 and 36 to operate those valves. Preferably, the characteristic is resistance or current through the conduit.

In operation, the system can be arranged as shown with valve 36 open and valve 22 closed. When the system is ready to dispense liquid into vial 10, valve 36 is closed and valve 22 is opened. Air pressure from source 20 forces liquid to flow through tube 18 into conduit 28. As soon as liquid occupies the region in the conduit between pipes 30 and 32, the resistance between those pipes drops because the liquid is, to some degree, electrically conductive. Control unit 38 responds to that change by closing valve 22 and opening valve 36. If desired, a small time delay can be introduced between the closing of valve 22 and opening of valve 36. With the closing of valve 22, flow of liquid from container 16 stops. Air from source 20 then passes through conduit 29 and blows the liquid in conduit 28 out of pipe 32 and into vial 10. The pressure of the air from source 20 is sufficiently small so that there is no splashing of liquid from the vial. The air flow can be terminated after a short interval by closing valve 22 or, if desired, the air flow can be continued to dry the conduit and thereby increase the accuracy of a subsequent measurement.

For a system in which the quantity of liquid to be dispensed is in the order of 10 $\mu$l, conduit 28 can have a diameter of 1 mm and a length sufficient to contain 10 $\mu$l between pipe 32 and the junction of the two conduits. A computer can easily be used to control the valves in response to the change of resistance or current flow between the electrodes. While the use of a computer would seem unnecessary with a single dispensing device, it is highly desirable when using multiple dispensing devices together as will be described.

Figure 2:
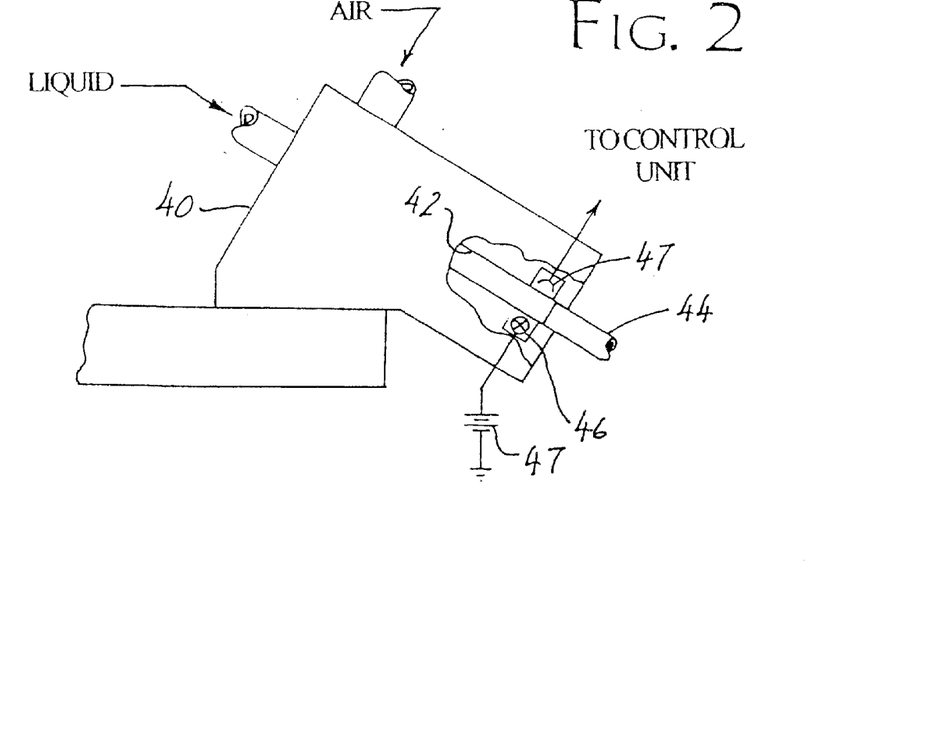
FIGS. 2 and 3 are schematic side elevations, in partial section, of further embodiments of dispensing devices in accordance with the invention.

FIG. 2 shows an alternative embodiment which uses an optical sensor rather than a current or resistance sensor to measure the quantity of liquid to be dispensed. Only the dispenser itself is shown in FIG. 2, the rest of the system being as shown in FIG. 1.

In FIG. 2, a dispenser body 40 has a conduit 42 connected to a reagent container 16 and to an output pipe 44 and also an air conduit connected to an air supply which can be the same as conduit 29 in FIG. 1. Near the inner end of output pipe 44 are two cavities adjacent and on opposite sides of conduit 42, one cavity containing a light source 46 and the other containing a photoresponsive device 47. The light source is connected to a source of electrical energy symbolized by the battery symbol 49 and the photoresponsive device is electrically connected to a control unit such as unit 20. When fluid enters conduit 42 under pressure, as described in connection with FIG. 1, and flows to the location of the light and photoresponsive device, control unit 20 detects the change in light transmission caused by the presence of the fluid and switches the conditions of the relays, terminating entry of fluid and blowing out of the outlet pipe the fluid between the air conduit and the light-photoresponsive device combination. The measured quantity is determined, as before, by the diameter and length of the conduit between those locations. Any combination of light and photoresponsive device capable of detecting the color or turbidity of the fluid from container 16 can be used.

As will be recognized, when the diameter of the fluid conduit 28 or 42 is of small diameter, on the order of 1 mm, the conduit behaves as a capillary and fluid therein does not flow under the force of gravity alone. Thus, any fluid left between the input tube feeding the fluid conduit and the outlet pipe stays in position until forced to move by air pressure or some other force.

It will be apparent from the above that the dispensing device described herein can be manufactured inexpensively and yet is capable of rapid and highly accurate dispensing of small volumes of liquid. It is contemplated that a single dispenser would be manufactured to dispense one predetermined volume of liquid and that if a different volume of liquid is to be dispensed, a dispenser designed for the new volume would be substituted. Alternatively, a dispenser can be controlled to dispense more than once into a specific vial if the vial is to receive a "double dose" of the substance.

Figure 3:
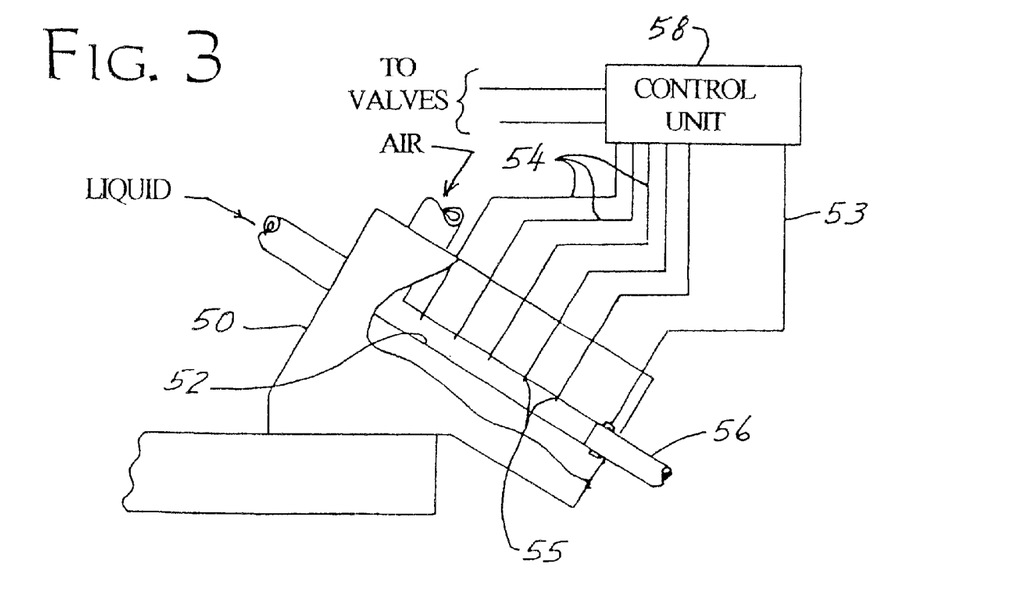

However, it is also possible with very little added complexity to make a dispenser capable of dispensing more than one measured volume of liquid. A device of this type is shown in FIG. 3 wherein a dispenser body 50 has a fluid conduit 52 passing therethrough and an air conduit arranged as in FIG. 1. A plurality of electrical wires 54 extend through body 50 and have exposed inner ends 55 protruding into the interior of conduit 52. The other ends or wires 54 are connected to inputs of a control unit 58. The exposed inner ends are spaced along conduit 52 at predetermined intervals selected to define a plurality of defined volumes between the wires and the inner end of an outlet pipe 56 which has a wire 53 connected between the pipe and an input of control unit 58. Control unit 58, preferably a computer, is programmed to respond when the fluid forms a connection between the outlet pipe and a selected one of wire ends 55, and to send control signals to the valves corresponding to valves 22 and 36 of FIG. 1. The valves are then switched to terminate flow into the fluid conduit and to blow out the measured quantity of liquid into a vial as previously discussed. As will be recognized, a plurality of optical sensors can be used instead of the wires.

Figure 4:
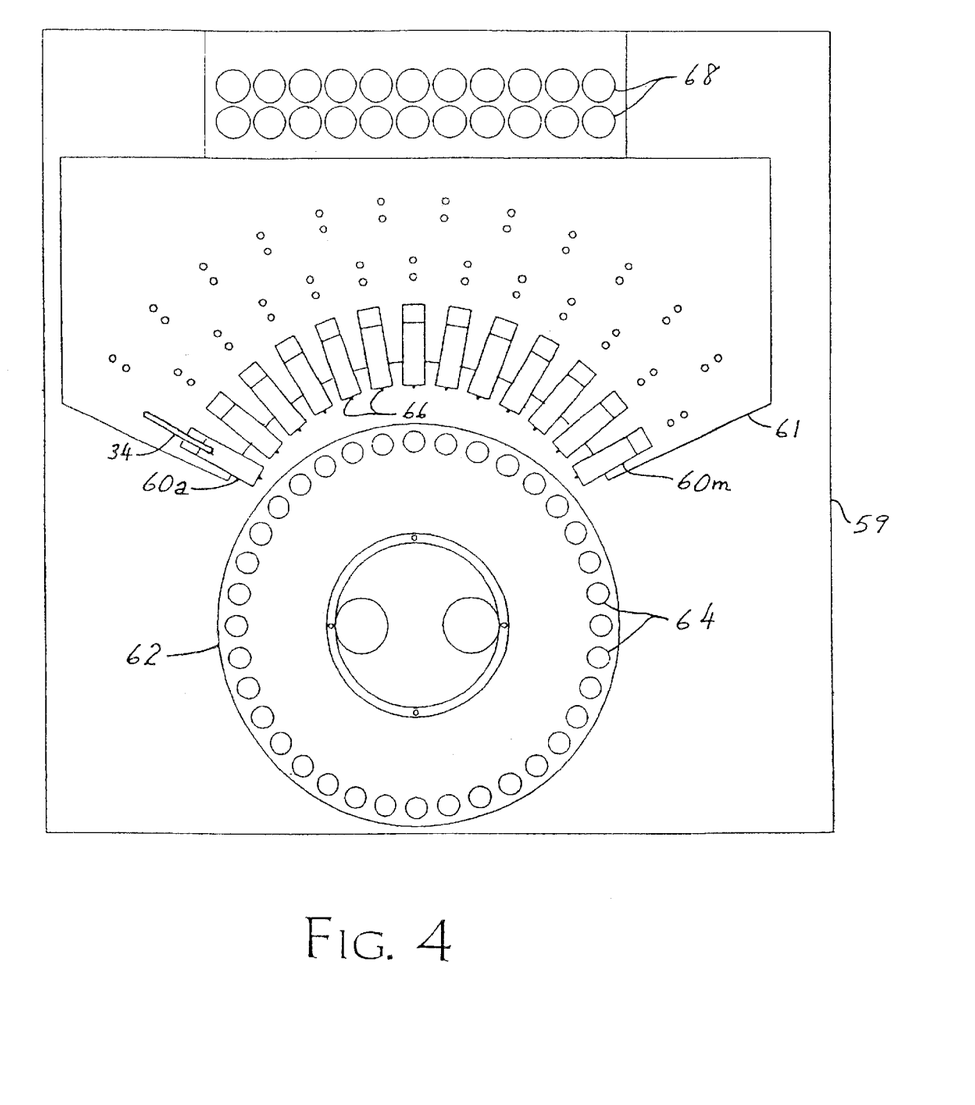
FIGS. 4 and 5 are schematic top plan views of a system in accordance with the invention including dispensing devices for adding substances to samples to be analyzed.
Figure 5:
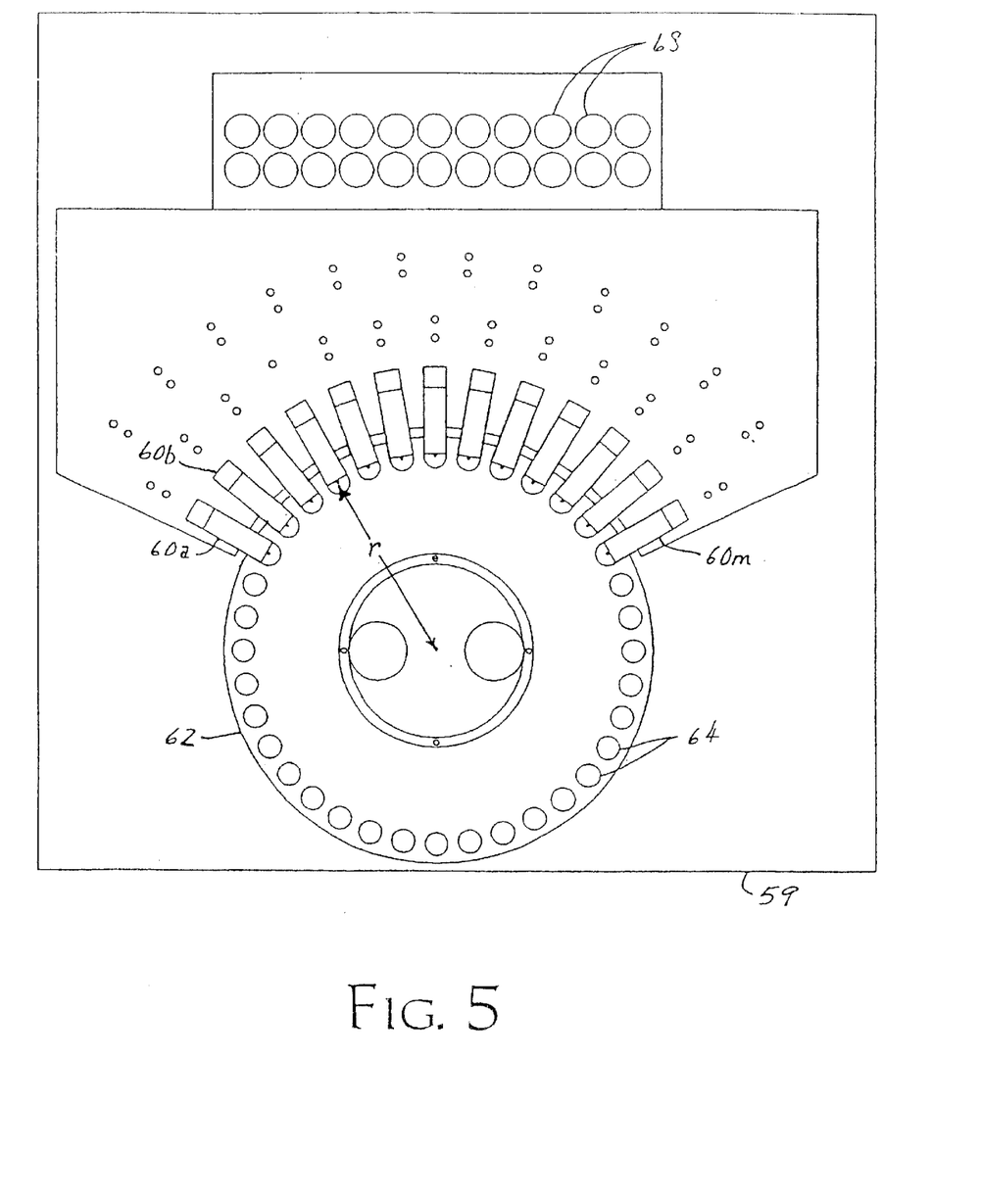

One embodiment of a system using a plurality of dispensers is illustrated in FIGS. 4 and 5 wherein a table 59 supports dispensers 60a through 60m arranged in a generally circular array on a shelf 61 around a rotatable carousel 62. Each dispenser can be constructed in accordance with any embodiment in the above description. Shelf 61 is movable toward and away from carousel 62 and is shown in an extracted position in FIG. 4 wherein receptacles in the carousel are loaded with a plurality of vials or test tubes 64 which are placed in the receptacles, uniformly spaced around the carousel, 36 vials being shown in FIGS. 4 and 5. After the carousel is loaded with the desired number of vials, the shelf is moved to the operating position shown in FIG. 5. Each dispenser has an outlet tube 66 and, in the operating position, the dispensers are positioned with their outlet tubes at one radius Γ from the center of rotation of the carousel so that liquid ejected from each dispenser enters one of the vials. Preferably, the angular separation between dispensers and between vials is either the same or one is an integral multiple of the other so that the carousel can be indexed around in steps which place vials immediately under output pipes in a known relationship.

Each vial is provided with a blood specimen or other substance to be analyzed. Each dispenser is connected to a container 68, corresponding to container 16 in the embodiment of FIG. 1, which contains a monoclonal antibody solution or some other solution which is to be added to selected ones of the vials. A plurality of containers 68 are supported in a rack 69 attached to the shelf. Tubes 30 and 34, only partly shown in FIG. 4, connect the dispensers with valves and the containers in the manner shown in FIG. 1 through pairs of holes 70 through shelf 61.

It should be emphasized that each dispenser is connected to one and only one container 68 and dispenses only one solution. Normally, each dispenser dispenses a different solution from each other dispenser, although this could be altered if some solution is to be dispensed in such volume that it is practical to dispense that solution from more than one.

It should also be mentioned that either the vial carousel or the dispensers can be constructed to rotate and that it would normally not be necessary in any installation to move both during the injection process. Because each dispenser is associated with its own supply of additive, moving either the dispensers or the vials is available as an option and can be determined on the basis of convenience is a particular structural arrangement. It is important only that relative motion be generated so that each dispenser can be positioned at each vial, as required by the desired addition of materials.

Figure 6:
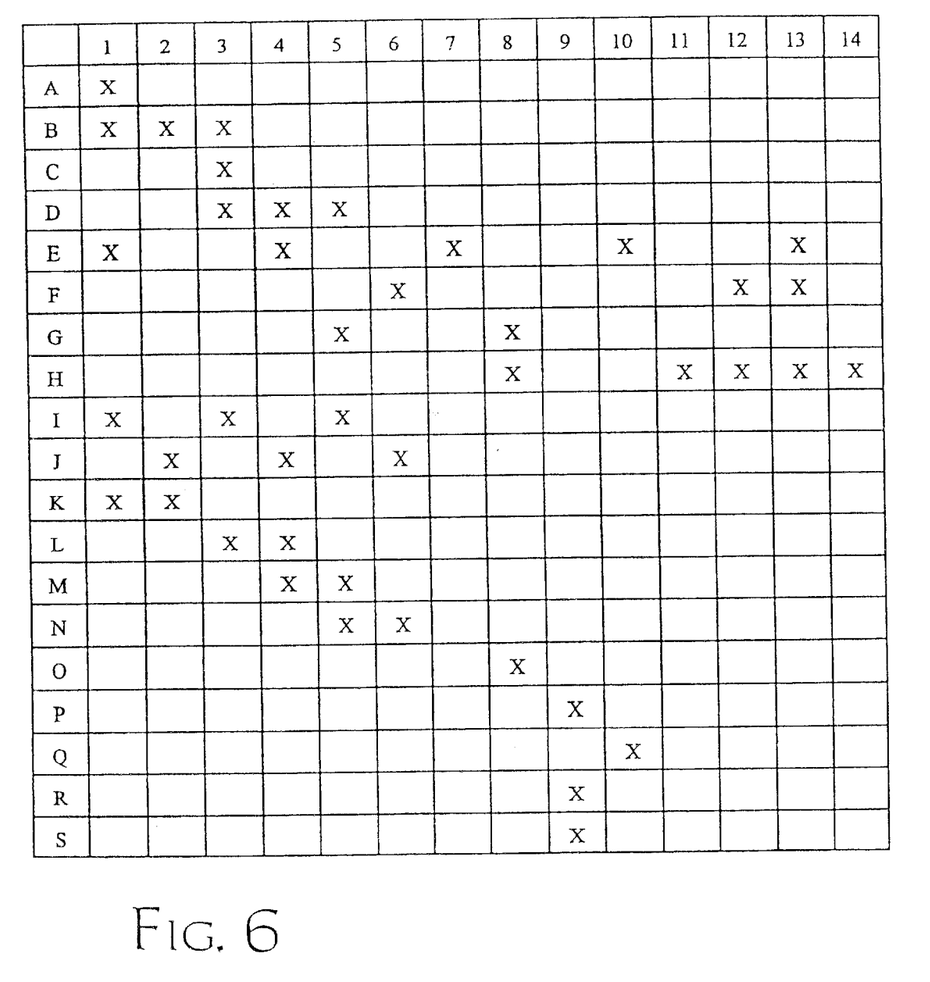
FIG. 6 is a diagram of a screen display of a computer used for controlling an apparatus in accordance with FIGS. 4 and 5.

Control of the addition of materials to the vials is preferably accomplished using a suitable programmed computer operating valves 22 and 36. An approach which has been found to be expeditious and which is simple to program and arrange begins with the assignment of a sequence of, e.g., letters to the vials and a sequence of numbers to the additive dispensers. A screen which appears somewhat like FIG. 6 is then generated with the letters along one axis and numbers along an orthogonal axis. By simply clicking on the intersection of a letter and a number, indicated in the figure by an X, a user can specify that the additive identified by the number is to be added to the vial identified by the letter.

Each dispenser then can be identified by a bar code or the like which is readable by a conventional bar code reader at the beginning of the process. The vials can be similarly identified or the vials can simply be loaded into the carousel at locations marked with the corresponding letter. It is then a simple matter for the computer to activate dispensing of additives into the proper vials in accordance with the selections made. From the start of dispensing to the completion thereof for a tray of 36 vials receiving from 3 to 6 additives each, the elapsed time is less than two minutes, not including any time which might be required for incubation which, of course, is the same for the systems of the present invention as for the prior art.

However, it will be recognized that the number of vials and additives which can be dealt with efficiently by the described system is essentially unlimited. By simply constructing a carousel with a larger diameter, a larger number of vials can be accommodated. Dispensers and vials can also be arranged in concentric rows.

Figure 7:
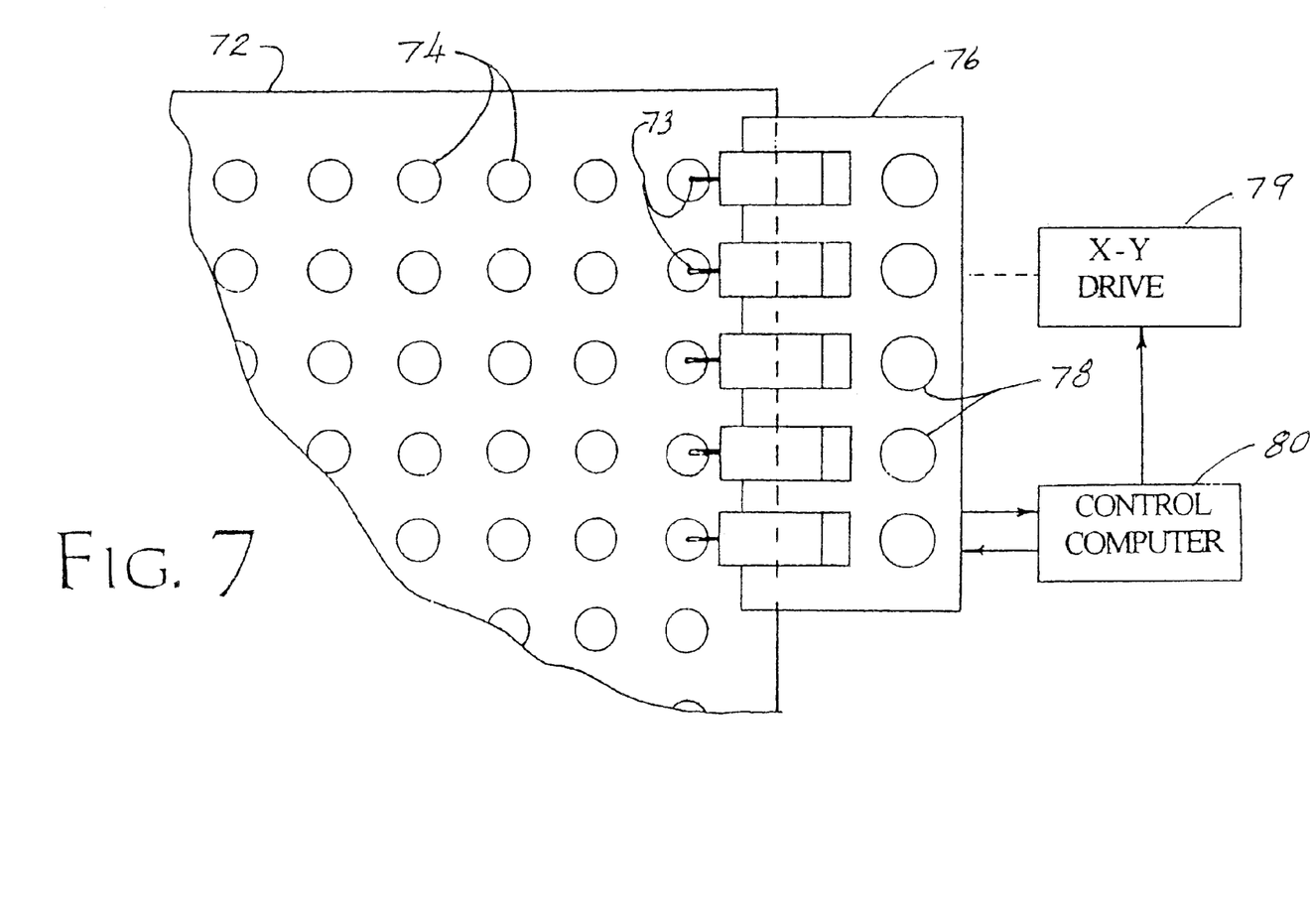
FIG. 7 is a schematic top plan view of another embodiment of a system in accordance with the invention for adding substances to samples to be analyzed.

Alternatively, a rectangular format can be used as illustrated in FIG. 7 wherein a rectangular tray 72 carries rows and columns of vials 74 with samples therein to be analyzed. An arrangement of any number of vials in each row and column can be used. Thus, an array of 20×20 vials, for a total of 400 vials, is quite possible. A carrier 76 supports a plurality of dispensers 77, five dispensers being shown in FIG. 7, although many more can be used. Carrier 76 also carries containers 78 with additive solutions therein, one for each dispenser. Carrier 76 is mechanically connected to a conventional X–Y drive 79 for moving the carrier and positioning it so that the outlet pipes 73 of the dispensers are over the upward open ends of the vials to inject additive solutions therein, as previously described. A control computer 80 is electrically connected to the components on the carrier and to the X–Y drive to receive information and control operation of valves such as valves 22 and 36, as previously described, and to control motion of the X–Y drive. The details of the tubes and electrical connections between the dispensers and the other components are as before and will not be repeated. It will also be recognized that carrier 76 can be held in a fixed position and the tray moved.

Operation of the apparatus of FIG. 7 involves stepwise movement of carrier 76 so that each dispenser rests above each vial for a short interval during which a measured quantity of liquid can be dispensed into the vial if the computer has been programmed to designate the vial to receive the substance being dispensed by the dispenser.

Figure 8:
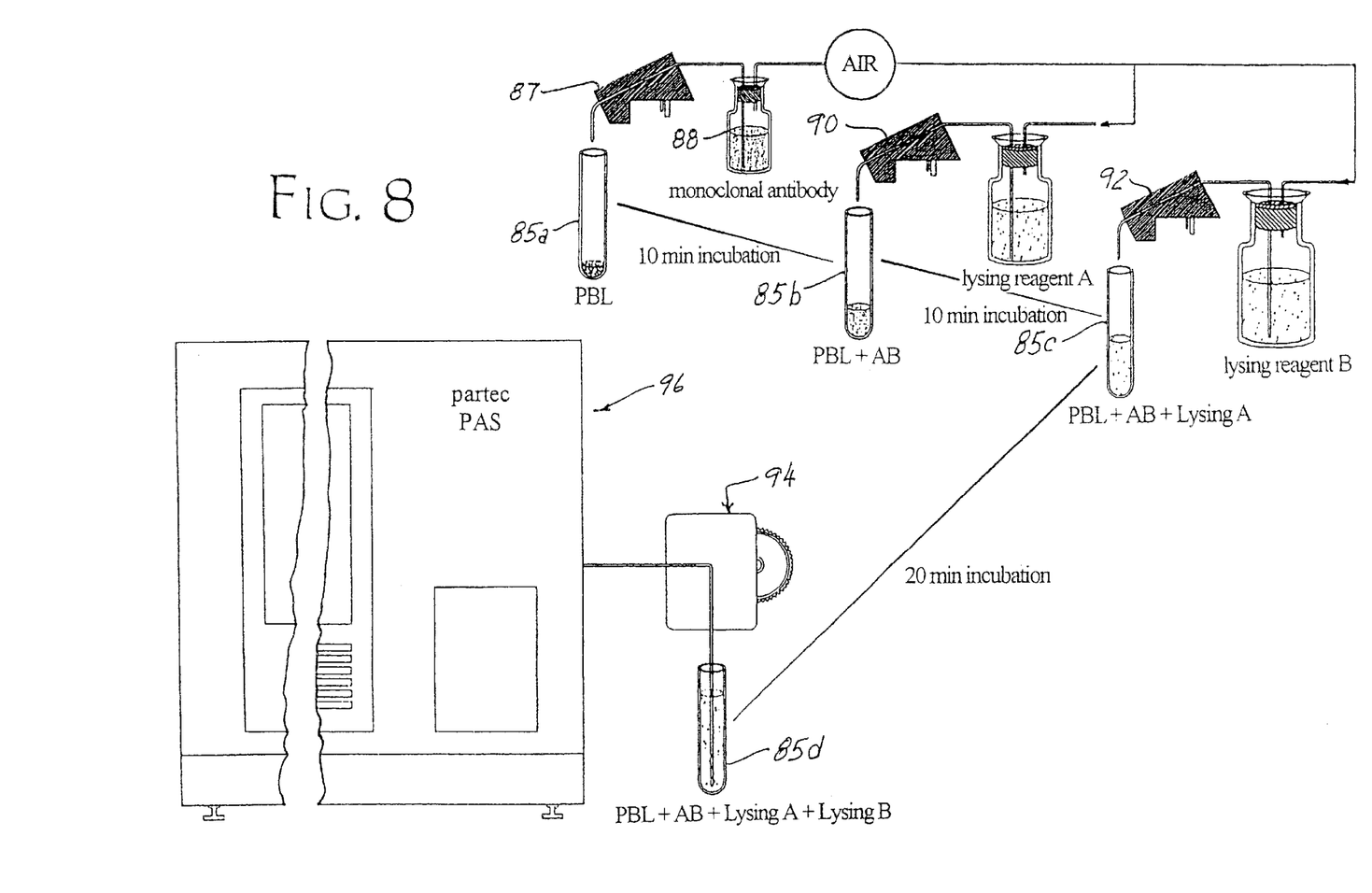
FIG. 8 is a schematic diagram illustrating steps in an example of a method according to the invention.

FIG. 8 schematically illustrates operation of the overall apparatus thus far described, including the automated analysis. For this example, sa single vial 85 is shown in multiple positions, identified by letter as it is processed, but it will be recognized that this vial is but one among numerous others in a carousel, for example, as described. Vial 85*a* begins with a blood sample PBL and is positioned under a first dispenser 87. Dispenser 87 is connected to a container 88 containing a monoclonal antibody AB and the container is pressurized by air as described in connection with FIG. 1. The control unit, now shown in this figure, causes dispenser 87 to dispense a measured quantity of the antibody into vial 85*a* and the vial is then incubated for 10 minutes. After incubation, the vial, now containing PBL+AB and identified as 85*b*, is positioned at a dispenser 90 from which is receives a preselected quantity of lysing reagent A. After another 10 minute incubation, vial 85*c* containing PBL+AB+Lysing A is positioned at a dispenser 92 from which it receives a quantity of Lysing reagent B. The vial 85*d* now contains PBL+AB+Lysing A+Lysing B and is incubated 20 minutes before analysis.

If necessary or desired, mixing can be accomplished between steps. This is usually determined by the specific staining technique used. If mixing is needed, this can be requested as part of the program and can be accomplished by repeatedly moving the carousel or tray back and forth using the carousel drive. Alternatively, other mixing techniques known in the art can be used.

An analysis machine, such as a Partec PAS, is mounted adjacent the carousel and has a sample gathering suction device indicated generally at 94 in FIG. 8. After the final incubation, the carousel is positioned adjacent the sample gathering device, the contents of the vial are sucked from the vial into the machine and analyzed and then discarded into a safe disposal facility. The analysis itself, which is not part of the present invention, results in data which are displayed or printed out, or both, in a manner which is well known in the field.

An important advantage of the apparatus of the present invention is that all of the processes beginning after placement of the samples into the vials are capable of being conducted automatically and can be performed in a completely closed environment, i.e., in a machine containing the vial carrier (e.g., a carousel) and the dispensers, so that workers in the vicinity are not exposed to harmful pathogens or the like during the processes.

Although the analysis itself is also done automatically, there has not been any apparatus available for completely automatically receiving and ingesting a sequence of samples for analysis. Thus, it has been necessary, even with the automatic dispensing described herein, to manually present each sample to the analysis machine.

Figure 9:
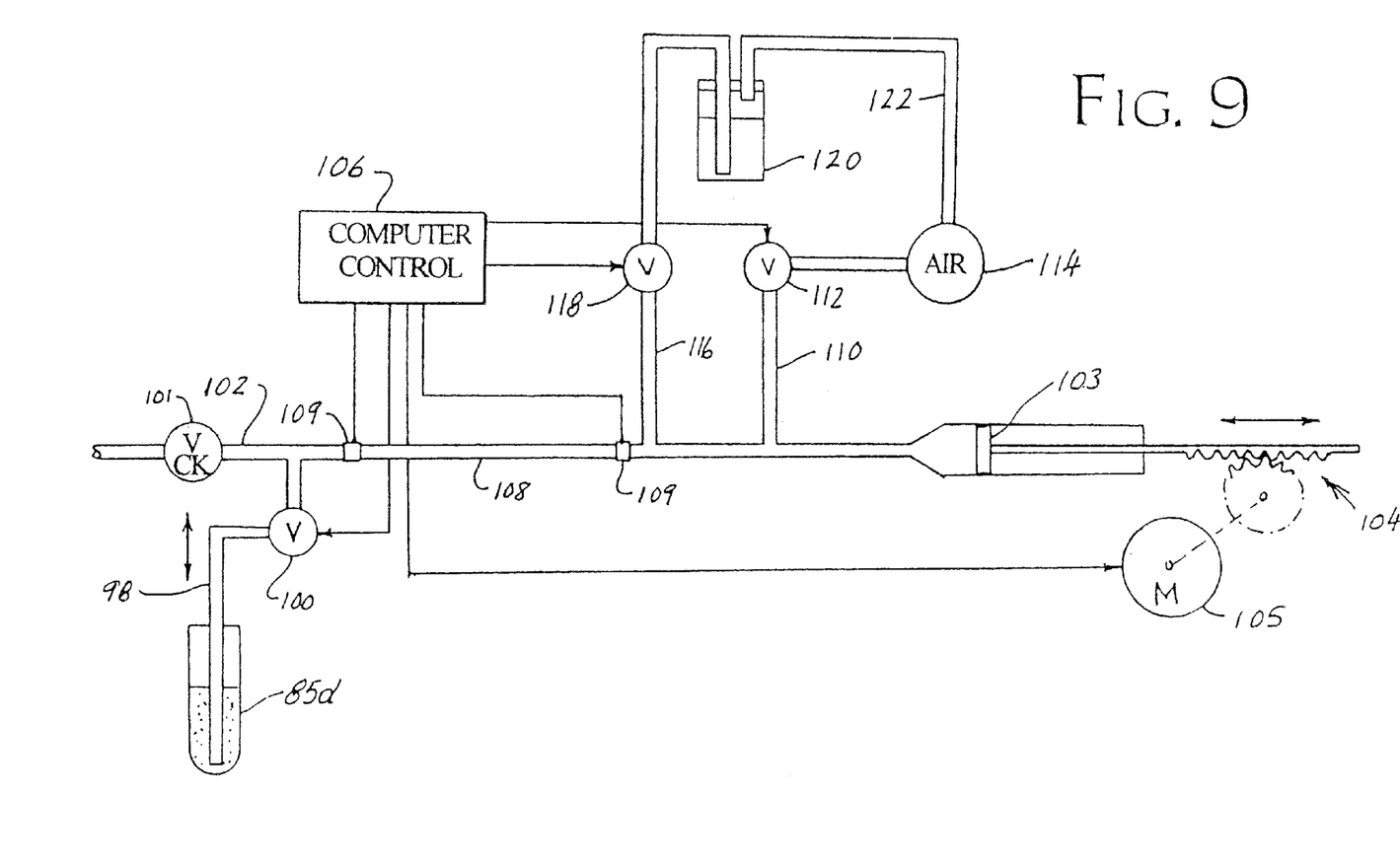
FIG. 9 is a schematic diagram of a system for automatically drawing samples into an analysis machine.

The present invention also includes an apparatus for automatically delivering a sequence of samples to an analysis machine 96 as shown in FIG. 8. As shown in FIG. 9, each sample is presented to the machine on, for example, a carousel at the end of a process such as described with reference to FIG. 8. A sample needle 98 is vertically movable, in a well-known manner, and can be automatically inserted into a vial 85*d* for the purpose of extracting the sample. In accordance with the present invention, the needle is connected through an electrically controllable valve 100 to a tube 102. One end of tube 102 is connected to the analysis portion of the machine, through a check valve 101, if necessary to prevent back flow, and the other end is connected to a syringe having a bidirectionally movable piston 103 operated by a drive mechanism 104 and motor 105 which is controlled by the computer control portion 106 of the machine.

A portion 108 of the tube 102 has electrically conductive portions 109 which are electrically connected to control 106 and enable the control to detect the presence of conductive fluid therein. When needle 98 is immersed in a vial, the computer opens valve 100 and energized motor 105, causing syringe piston 103 to be withdrawn to the right as shown in the figure, sucking the fluid sample into tube 102 until conductivity is detected in tube portion 108 at which time the piston is stopped and valve 100 is closed.

A tube 110 is connected from tube 102 through an electrically controllable valve 112 to a source 114 of air under pressure. Valve 112 is electrically connected to control 106 and is closed during the process of moving the piston to suck the sample into tube 102. A tube 116 is connected from tube 102 through an electrically controllable valve 118 to a reservoir 120 of washing fluid which is pressurized through a tube 122 connected to air source 114. Valve 118 is controlled by the computer control and is also closed while a sample is being sucked into tube 102.

When the sample is in tube 102 and valve 100 is closed, valve 112 is opened, allowing air under pressure to enter tube 102, pressing the sample through the check valve and into the analysis machine. The machine itself and the analysis process is not part of the present invention and will not be further described.

Alternatively, piston 103 can be moved to the left, causing air under pressure to move the sample into the machine. However, the use of pressurized air from a source such as 114 is preferred because the length of the stroke of piston 103 limits the amount of pressure which can be applied to move the sample and is likely to be a slower technique. In either case, the piston is returned to is left-most position to be ready for a new sample.

A washing procedure is necessary after each sample has been processed as described. Reservoir 120 contains a clean washing solution. Valve 112 is again closed and valves 118 and 100 are opened, allowing the washing solution under pressure from source 114 to move through tube 116 and into tubes 102 and 98, flushing the regions of the tubing through which the sample had passed. The flushing liquid can be collected in the same vial from which the sample was taken or can be collected in a separate vial provided for that purpose.

The provision of a totally automatic system which handles the samples from the time they are inserted in the vials through the entire additive and analysis process has numerous advantages predominantly including safety. The entirely automatic handling allows the entire procedure to be conducted in a closed chamber containing the machines without handling or exposure of personnel to any of the substances.

In addition, the apparatus described herein has very significant advantages of speed achieved because of the use of individual dispensers for each chemical additive and parallel dispensing into the sample vials to a significant degree. Washing of the dispensing tip is eliminated because each tip is only used for one chemical. This also eliminates, or at least greatly reduces, lost volume of monoclonal antibody solution which is highly expensive. Since the additive containers are closed, rather than standing open as with prior art devices, there is no significant evaporation of the chemicals. Accuracy of dispensing due to the electronic volume control is unmatched by any known system and repeatability is extremely precise. Tests have shown that in a series of 25 volumes intended to be of 18 $\mu$l each dispensed by a device in accordance with the invention, the volumes dispensed were within over 98% of each other, a result obtainable with no known device.

In addition, the system allows a nearly unlimited number of additives, greatly reduced time, and dispensing of very small volumes, selectable by choosing a suitable dispensing head. Furthermore, the path for conveying sample vials can be of nearly any shape, allowing the used of conveying devices following an irregular path between sample insertion and analysis with the dispensing heads positioned along the way. For the first time, it is conceivable to do testing in a substantially continuous process, not only in batches as has been necessary in the past.

While certain advantageous embodiments have been chosen to illustrate the invention, it will be understood that various modifications can be made therein without departing from the scope of the appended claims.

What is claimed is:

1. An apparatus for dispensing a measured quantity of a liquid comprising a container holding a quantity of liquid to be measured and dispensed;

a conduit having an inlet end and an outlet end and including a measuring section having a predetermined volume and a dispensing tip at said outlet end;

sensor means for determining when said measuring section is substantially full of liquid;

a passage for delivering liquid from said container to said conduit inlet end;

a first source of air under pressure for forcing liquid from said container to said conduit;

a first valve in said passage;

a second source of air under pressure connected to said conduit;

a second valve controlling delivery of air to said conduit from said second source; and control means connected to said sensor means and to said first and second valves for sequentially closing said second valve and opening said first valve to cause flow of liquid from said container to said conduit until said sensor means determines that said measuring section is full of said liquid, and then closing said first valve and opening said second valve to admit air to said conduit, thereby expelling said measured quantity of liquid from said dispensing tip.

2. An apparatus according to claim 1 wherein said conduit comprises a body of electrically nonconductive material having an axial opening therethrough, and said sensor means comprises first and second electrodes mounted at axially spaced locations along said opening, and means for detecting a change in an electrical characteristic between said electrodes indicating the presence of liquid.

3. An apparatus according to claim 2 wherein said axial opening has a substantially constant cross-sectional area, whereby said measured volume comprises said cross-sectional area multiplied by axial spacing of said electrodes.

* * * * *

UNITED STATES PATENT AND TRADEMARK OFFICE
CERTIFICATE OF CORRECTION

PATENT NO.    : 6,371,331 B1
DATED         : April 16, 2002
INVENTOR(S)   : Gohde et al.

Page 1 of 1

It is certified that error appears in the above-identified patent and that said Letters Patent is hereby corrected as shown below:

Column 3,
Line 50, after "conduit", insert -- 29 --.

Column 4,
Line 2, delete "pen" and insert -- open --.

Column 7,
Line 22, delete "sa" and insert -- a --.

Signed and Sealed this

Twenty-fourth Day of September, 2002

Attest:

Attesting Officer

JAMES E. ROGAN
Director of the United States Patent and Trademark Office